United States Patent
Robins et al.

(10) Patent No.: US 6,909,027 B1
(45) Date of Patent: Jun. 21, 2005

(54) METHOD OF FORMING AN IN-SITU FILM DRESSING AND THE COMPOSITION OF THE FILM-FORMING MATERIAL

(76) Inventors: Perry Robins, 330 E. 38th St., suite 41N, New York, NY (US) 10016; Joseph G. Sant'Angelo, 568 Parkside Ct., Allentown, PA (US) 18104

(*) Notice: Subject to any disclaimer, the term of this patent is extended or adjusted under 35 U.S.C. 154(b) by 0 days.

(21) Appl. No.: 10/178,522

(22) Filed: Jun. 25, 2002

Related U.S. Application Data

(60) Provisional application No. 60/311,948, filed on Aug. 13, 2001.

(51) Int. Cl.[7] ............................................. A61F 13/00
(52) U.S. Cl. .......................................... 602/52; 602/42
(58) Field of Search ............. 602/41–59; 606/213–216

(56) References Cited

U.S. PATENT DOCUMENTS

| | | | | |
|---|---|---|---|---|
| 4,142,021 A | * | 2/1979 | Dixon et al. | 428/412 |
| 4,833,036 A | * | 5/1989 | Cannarsa et al. | 428/412 |
| 5,713,842 A | * | 2/1998 | Kay | 602/57 |
| 5,725,491 A | * | 3/1998 | Tipton et al. | 602/43 |
| 6,034,113 A | * | 3/2000 | Hewawasam et al. | 514/364 |
| 6,084,037 A | * | 7/2000 | Shimizu et al. | 525/476 |

* cited by examiner

*Primary Examiner*—Kim Lewis

(57) ABSTRACT

This invention relates to the application of a film covering produced from a unique family of polymers, polyalkylene carbonates for optimizing wound care treatment.

17 Claims, No Drawings

METHOD OF FORMING AN IN-SITU FILM DRESSING AND THE COMPOSITION OF THE FILM-FORMING MATERIAL

This application claims the benefit of Provisional Application No. 60/311,948 filed Aug. 13, 2001.

This invention pertains to a wound care system, including a unique dressing and the composition constituting the dressing.

BACKGROUND OF THE INVENTION

This invention relates to wound care covering both external wounds (skin, etc) as well as internal wounds (organs, etc). There are many aspects to wound care, both medical and economic. The shorter the treatment time, the more economical the process and the greater the patient comfort. Treatment and nursing costs are up to 10 times higher than supply costs. Some complications that increase treatment time are infections, non-optimal wound care dressing, longer healing and closure times. These are affected by the wound care system used. The most common wound dressings have been gauze and tape. Subsequently, multi-layered systems have been designed with a film backing. Liquid bandages that provide a film covering of the wound have been developed. These wound coverings provide some of the desired protection to wounds, but do not provide the optimal environment for enhanced wound healing and minimal scarring.

Gauze dressings may not completely protect the wound from water, bacteria, dirt, external oxygen and other foreign matter. Gauze can stick to wounds causing wound damage during dressing changes, increasing the probability of infection and lengthening healing time.

Multi-layered dressings are an improvement over gauze dressings, however they can be stiff and bulky, can be susceptible to channeling permitting bacteria and foreign material to enter wounds. Generally these dressing have a layer for absorbing wound exudate and need to be changed during wound healing. Damage can occur to the wound due to sticking of the dressing to the wound. These multi-layered dressings can have a film backing. Typically polyurethane is used. It does not provide the desired barrier to external oxygen to protect the wound from the external oxygen during the early stages of healing. Some multi-layered dressings may provide some low level of oxygen barrier due to the dressing and its thickness.

Liquid bandages are usually polymer solutions dissolved in organic solvents. The solution is applied directly to the wound, the solvent is evaporated and or precipitated, or the solution is coagulated in situ leaving a film covering over the wound. These films can be nitrocellulose polymers or cyanoacrylates. These films do not provide oxygen barrier properties to the wound site. Since they are not elastomers, they do not provide elasticity and recovery to the film. Due to their high softening temperatures they do not permit the film to flow as a result of the skin/body heat. The nitrocellulose films have a tendency to form cracks when placed on a site that is flexing, eg. Base of the thumb or any other anatomical body part that has movement. These cracks then destroy the protective covering of the wound. These films can also give off undesirable chemical oders. None of the above wound coverings provide all of the desired combination of properties needed for enhanced wound healing such as oxygen barrier, elasticity and recovery, low glass transition temperatures for improved conformity to the site, non-sticking to the wound due to enzyme degradation of the polymer at the wound site giving off carbon dioxide and water.

Other polymeric film coverings may be used such as polyvinylidene chloride and polyvinyl alcohol which can be oxygen barriers. However they have critical limitations. They are not elastomeric polymers with low glass transition temperatures therefore wound not provide films with the needed elasticity and recovery. Polyvinyl alcohol is water soluble and when wet loses its oxygen barrier properties. Polyvinylidene chloride being primarily a crystalline polymer has a high temperature melting and softening point therefore skin and body temperatures are too low to promote flow of the polymer to provide optimum conformity to anatomical body shapes.

Polycarbonates have been given as one of many polymers to be used as a film. They do not work as is taught in this application. Polycarbonates are different polymers than polyalkylene carbonates.

Almost every phase of the healing process is significantly affected by products used to cover the wound, and the resulting environment. (Nemeth A J et al. "Faster healing and less pain in skin biopsy sites treated with an occlusive dressing. Arch Dermatol 1991; 127:1679–83)

In wounds, new blood vessels grow from zones rich in oxygen toward those with less oxygen.(Knighton D et al. "Oxygen tension regulates the expression of angiogenesis factor by macrophages". Science 1983 221:1283–5) Normal tissue has an oxygen tension of about 40 mm of Hg. Angiogenesis are stimulated at about 1–10 mmHg relatively hypoxic conditions. (Hunt T K, et al. "Wound microenvironment in Cohen IK et al. (eds) Wound healing: Biochemical and Clinical Aspects." Philadelphia, W B Saunders, 1992, pp 274–281); and (Pai MP et al. "Effect of varying oxygen tensions on healing of open wounds." Surg Gynecol Obstet 1972; 135: 756–758); and (Storch T G et al. "Oxygen concentration regulates the proliferation responses of human fibroblast to serum and growth factors. Exp Cell Res 1988; 175: 317–325)

Oxygen impermeable dressings to outside oxygen cause angiogenesis to proceed most rapidly. Early oxygen deprevation and later oxygen supplemation are conducive to healing. Reduced wound pH also contributes to angiogenisis. A low pH is maintained by preventing wound tissues from losing all of their carbon dioxide.

Some of the problems related to certain wound care systems in prior art methods include:
- non-optimal (higher) gaseous oxygen environment around the wound as a result of wound dressings permitting outside oxygen to enter the wound area in the early stages.
- lack of proper (adequate) moisture.
- bacterial invasion into wound area due to poor bandage adhesion and or coverage, and film coverings which are not elastic and therefor form cracks, channels and wrinkles leading to the wound.
- non-optimal removal of exudate related to insufficient water vapor transmission from the wound.
- improper mechanical pressures on wound.
- gauze bandages can be contaminated from handling, stick to wounds and cause damage to the cells in the healing process during dressing changes by peeling off epidermal cells and interfering with healing
- stiff dressings which maybe flexible but are not elastic so as to conform tightly to body shapes during movement.

loss of carbon dioxide from wound tissues leading to high ph and alkalosis
skin sensitivity to tapes causing rashes
chemical odors of varying degrees
other film dressings do not incorporate all of the key properties needed in a solitary film.

This invention provides an interactive wound care system that solves the above problems. The system provides an occlusive covering and interaction with the wound during the healing process, providing the optimum gas and liquid environment for enhancing wound healing, improving patient comfort and reducing costs.

BRIEF SUMMARY OF THE INVENTION

Enhanced wound healing and minimal scarring occur when the wound covering permits the required concentration around the wound of oxygen, water moisture, exudate, carbon dioxide and bacteria.

A recently developed family of polymers, called polyalkylene carbonates(PAC) are utilized to design the optimum environment in and around the wound. These polymers are produced by reacting carbon dioxide with epoxides. (Inoue S, "Organic and Bio-Organic Chemistry of Carbon Dioxide" Halsted Press, New York, pp167–176, 1982) The resulting properties of the polymer are a function of the epoxide selected.

Polymers can be produced with properties that range from soft elastomeric with low glass transition temperatures (18 C to 25 C to 40 C), to hard stiff polymers with high glass transition temperatures eg 132 C Intermediate properties can be produced by chemical(terpolymers) and physical (blends) means. These polymers then can be selected to provide various degrees of oxygen barrier to the wound from exterior oxygen, as well as carbon dioxide transmission from the wound for enhanced wound healing.

Films made from these polymers adhere to skin forming a barrier to outside dirt, water and bacteria and allow water vapor permeability from the wound permitting excess exudate and bacteria to also leave the wound, through evaporation, reducing wound pressures and infections.

These films will not adhere to wounds thereby permitting frequent dressing changes without disturbing the normal healing process of the wound. Additionally, these polymers can be dissolved in a number of biologically acceptable solvents providing solutions of one or more polyalkylene carbonates with one or more solvents to permit designing the appropriate film, foam, or gel composition. These polymers can also be produced as water based emulsions. These solutions or emulsions can then be brushed or sprayed around the wound, forming a conforming protective and interactive film to enhance wound healing. Other methods of application such as gels from squeeze tubes, melt formed films or liquid solutions rolled on or spread with a squeegee or spatula can be used. Other additives may be dissolved or dispersed in these solutions to permit design of a chemical medical system to optimize wound healing. Wounds may first be pretreated with medical additives etc. then sprayed over with a protective film covering etc. The object of this invention is to solve problems inherent in other wound care dressings by properly designing the appropriate polyalkylene carbonate polymer or combination of polyalkylene carbonate polymers to solve the problems of current dressings.

Physical chemical properties of one or more of this family of polyalkylene carbonate polymers which can be selectively utilized are:

clear, amorphous, thermoplastic
glass transition temperatures range from 18 C to 132 C
excellent adhesion to skin, non-sticking to wound
soft elastomeric polymers with good recovery, to hard engineering polymers
enzyme degrades or burn cleanly into primarily carbon dioxide and water
excellent oxygen barrier
semi-permeable to water vapor
potentially low cost
quick drying with no oder
soluble in a wide range of solvents from low boiling to high boiling.
low glass transition temperature of polyethylene carbonate, 25 C makes for a soft, flexible and elastic bandage, which is softened by the skin and body temperature promoting conformability to body shapes in motion.
controllable oxygen permeability
carbon dioxide semi-permeability
barrier to out side water, dirt, bacteria
can be produced as water based emulsions
excellent self adhesion of films

DETAILED DESCRIPTION OF THE INVENTION

To use this invention, the polyalkylene carbonate polymer or polymers are applied to animal tissue (eg. over a wound) in a fluid form. Thus for example the polyalkylene carbonate can be dissolved in a biocompatible solvent or solvents. Some of the solvents that can be used are methylene chloride, dichloroethane, propylene carbonate, dimethylformamide, N-Methyl pyrrolidone, acetone, ethyl acetate, tetrahydrofuran, methyl ethyl ketone as well as other ketones, esters, ethers, etc. The polymer concentration is a function of the delivery system.

The wound is first cleaned, and then any of the following methods of application are used:

If a spray can (aerosol) or bottle spray are used then a lower concentration of polymer is used to provide the proper viscosity for spraying and film forming on and around the wound. This concentration would also be a function of the solvent selected and molecular weight. Polymer concentration 5–35%.

If a brush, Q-tip, eye dropper or rod are used then an intermediate polymer concentration is used with proper viscosity to prevent the solution from running away from the wound. Polymer concentration 5–50%.

If a gel or squeeze tube is used, the polymer concentration could be higher. The gel could be applied directly and spread out to form a film on and around the wound. Polymer concentration 20–60%.

If a melt film is to be used, dispensed from a melt film forming device, the polymer concentration could be very high eg. 100% polymer minus any additives, eg, absorbants, moisturizers, medications, plasticizers, etc.

If an emulsion is used eg, water based emulsion the polymer concentration would be maximized based on other chemicals in the system. Polymer concentration 10–60%.

The film produced from any of the above methods has excellent adhesion to itself. Therefore films can be made to completely wrap around certain body parts, and made to adhere to itself. Spraying on a film can provide better protection around wounds in odd shaped (irregular shapes) of the body, by providing a complete seal around the wound.

The use of polyethylene carbonate with excellent oxygen barrier properties, low Tg of about 25 C, very high elongation and recovery, flexibility and elasticity provides excellent conformity and protection to irregular body shapes. The low Tg, permits body skin temperatures to soften the polymer further and better conform to irregular shapes, increasing the patients comfort and providing excellence protection to the wound. Film thickness can be 0.25–3.0+mils.

In the early stages of healing in certain types of wounds, external oxygen is not desirable. By blocking external oxygen and permitting the internal oxygen in blood vessels from within to assist in the wound healing, wounds heal more rapidly and with less scarring. Prior patents did not recognize his important role of oxygen exclusion. They taught the opposite, "an adequate exchange" of oxygen and or films that are "semi-permeable" to oxygen. Kay, U.S. Pat. No. 5,713,842, teaches allowing "the free diffusion of oxygen, water vapor, and other gases through their molecular matrices", with polyurethane films being preferred. Tipton et al. U.S. Pat. No. 5,725,491 teaches "it is preferred that the size and number of pores of the film dressing facilitate diffusion of nutrients, oxygen, water and biologically active agents"

Examples in prior patents of polymers that can be used do not include polyalkylene carbonates.

Wounds treated with oxygen permeable films produce lower recovery rates. Occlusive dressings have a lower infection rate than non-occlusive dressings. Therefore using polyethylene carbonate film as the polymer of choice we combine:
- oxygen barrier
- low Tg, about 25 C, allowing body temperatures to soften the polymer and flow to produce excellent conformity to irregular body surfaces, excellent adhesion to skin around the wound, and improved comfort for the patient.
- foreign material barrier
- water proofing from external water
- elastomeric properties-non cracking film from surface movement
- good insulating properties
- one component system—easy to apply, may be sold over the counter
- good skin adhesion—keep out bacteria and foreign matter
- excellent self adhesion—for complete wrap arounds or multiple layers if needed
- clear film for wound observation if desired
- enzyme degradability of polymer at wound/film surface interface forming carbon dioxide and water to enhance bandage removal and wound healing.
- oil resistant, acid and base resistant, therefore not affected by body oils or fluids
- abrasion resistant, not easily damaged by external forces
- chemical/medical additives—good bonding, dispersion or solution
- does not stick to wounds, permitting frequent bandage changes without damaging repair cells in the wound, which reduces odors and promotes healing
- film is permeable to water vapor, helping to remove exudate and bacteria
- semi permeable to carbon dioxide helping to maintain a low ph and preventing alkalosis
- with methylene chloride as the solvent, film is quick drying and has no residual odor
- indefinite shelf life
- low cost wound cover A preferred method of using this invention is to produce a 10–15% solution of polyethylene carbonate in methylene chloride. The wound is washed or pretreated, then dried. It is then coated with the polymer solution, brush or spray, and allowed to dry. The drying process is a matter of minutes due to the low boiling point of the solvent 39.7 C. The skin temperature is about 33 C, body temperature about 37 C, promoting evaporation of the solvent, and flow of the polymer which has a glass transition temperature of about 20–25 C. The wound healing process is observed through the clear film. If dressing changes are required, the film is easily removed and new film applied. The film is removed when the healing is completed.

In certain other type wounds or in the later stages of certain wounds, external oxygen may be desired and therefore polypropylene carbonate would be used since it is not a good oxygen barrier. By blending polypropylene carbonate and polyethylene carbonated either physically or chemically (terpolymer), intermediate properties can be obtained to optimize wound healing., as a function of wound type.

There are no other polymer families that can incorporate the unique broad range combination of physical/chemical properties obtainable with this new family of polymers, polyalkylene carbonates. They can be "tailored" to fit the application, thereby providing a total healing system that enhances wound healing, reduces scarring adds to patient comfort and reduces costs.

Wound healing is a complex process. Significant, valuable medical knowledge has been developed which can enhance wound care. Polyalkylene carbonate polymers have a broad range of properties that can effectively be utilized with the current medical knowledge to produce a new generation of wound coverings. They also have the potential to be tailored to meet new medical requirements as new knowledge in wound care is developed.

We claim:

1. The method of forming an in situ film dressing on animal tissue which comprises preparing an application fluid comprising polyalkylene carbonates, applying the fluid to animal tissue and thereby forming a film on the animal tissue.

2. The method of forming an in situ film dressing of claim 1 wherein the polyalkylene carbonate is placed into fluid form by raising the polyalkylene carbonate to a temperature at least as high as its glass transition temperature and applying the fluid polyalkylene carbonate to the animal tissue.

3. The method of forming an in situ film dressing of claim 1 wherein the polyalkylene carbonate is placed in fluid form by forming a suspension of the polyalkylene carbonate in a biocompatible medium, applying the fluid polyalkylene carbonate to the animal tissue and evaporating the biocompatible medium.

4. The method of forming an in situ film dressing of claim 3 wherein the content of the polyalkylene carbonate in the suspension is from about 10% to about 60% by weight and the suspension is applied onto the animal tissue.

5. The method of forming an in situ film dressing of claim 1 wherein the polyalkylene carbonate is placed in a fluid form by forming an emulsion of the polyalkylene carbonate in a biocompatible medium, applying the fluid polyalkylene carbonate to the animal tissue and evaporating the biocompatible medium.

6. The method of forming an in situ film dressing of claim 1 wherein the polyalkylene carbonate is placed in fluid form by forming a solution of the polyalkylene carbonate in a biocompatible solvent, applying the fluid polyalkylene carbonate solution to the animal tissue and evaporating the biocompatible solvent.

7. The method of forming an in situ film dressing of claim 6 wherein the content of the polyalkylene carbonate in the solution is from 5% to 50% by weight and the solution is applied onto the animal tissue.

8. The method of forming an in situ film dressing of claim 1 wherein the alkylene component of the polyalkylene carbonate contains from two to nine carbon atoms.

9. The method of forming an in situ film dressing of claim 1 wherein the alkylene component of the polyalkylene carbonate is selected from the group consisting of ethylene, propylene and butene.

10. A material for forming a film dressing on animal tissue which comprises a polyalkylene carbonate having a glass transition temperature (Tg) of from about 18 to about 40° C. in a fluid form, which fluid polyalkylene carbonate adheres to animal tissue.

11. The material of claim 10 wherein the polyalkylene carbonate is placed in fluid form by raising the polyalkylene carbonate to a temperature at least as high as its glass transition temperature.

12. The material of claim 10 wherein the polyalkylene carbonate is placed in a fluid form by forming a suspension of the polyalkylene carbonate in a biocompatible medium.

13. The material of claim 10 wherein the polyalkylene carbonate in fluid form is a solution in a biocompatible solvent.

14. The material of claim 13 wherein the alkylene component of the polyalkylene carbonate is selected from the group consisting of ethylene, propylene, and butene.

15. The material of claim 13 wherein the biocompatible solvent for polyethylene carbonate comprises methylene chloride.

16. The material of claim 13 wherein the biocompatible solvent for polypropylene carbonate comprises acetone.

17. The material of claim 13 wherein the polyalkylene carbonate is polyethylene carbonate having a glass transition temperature of from about 20 n to about 25° C., the biocompatible solvent is methylene chloride and the polyethylene carbonate is present in the solution in a concentration of from about 10 to about 15%.

* * * * *